United States Patent [19]

Balkenhohl et al.

[11] Patent Number: 5,728,876
[45] Date of Patent: Mar. 17, 1998

[54] RESOLUTION OF THE RACEMATES OF PRIMARY AND SECONDARY AMINES BY ENZYME-CATALYZED ACYLATION

[75] Inventors: Friedhelm Balkenhohl, Limburgerhof; Bernhard Hauer; Wolfgang Ladner, both of Fussgoenheim; Uwe Pressler, Altrip; Christoph Nübling, Hassloch, all of Germany

[73] Assignee: BASF Aktiengesellschaft, Ludwigshafen, Germany

[21] Appl. No.: 596,238

[22] PCT Filed: Sep. 16, 1994

[86] PCT No.: PCT/EP94/03102

§ 371 Date: Mar. 11, 1996

§ 102(e) Date: Mar. 11, 1996

[87] PCT Pub. No.: WO95/08636

PCT Pub. Date: Mar. 30, 1995

[30] Foreign Application Priority Data

Sep. 25, 1993 [DE] Germany ............ 43 32 738.9

[51] Int. Cl.$^6$ .................... C07C 231/02; C07C 231/16
[52] U.S. Cl. .................... 564/136; 435/131; 435/195; 435/196; 435/280; 546/247
[58] Field of Search .................. 435/280, 131, 435/195, 196; 546/247; 564/136

[56] References Cited

U.S. PATENT DOCUMENTS 5,057,607  10/1991  Zmijewski, Jr. et al. .......... 540/364

FOREIGN PATENT DOCUMENTS 443 406      8/1991   European Pat. Off. .
WO 90/14429  11/1990  WIPO .
WO 91/19002  12/1991  WIPO .

OTHER PUBLICATIONS

Enzymatic Aminolysis . . . Gotor et al., Tetrahedron, vol. 47, No. 44, pp. 927–2914, 1991.

Chem Abst. 115:278181j, Fermentations, vol. 115, 1991, p. 847.

Enzymatic Synthesis of Amides . . . Brieva et al., J. Chem So., 1990, pp. 1386–1387.

Lipase–Catalyzed Synthesis . . . , Tetrahedron, vol. 4, No. 6, pp. 1105–1112, 1993, Quiros et al.

*Primary Examiner*—Shailendra Kumar
*Attorney, Agent, or Firm*—Keil & Weinkauf

[57] ABSTRACT

A process for producing optically active primary and secondary amines from the corresponding racemates is characterised in that (a) a racemic amine is enantioselectively acylated in the presence of a hydrolase with an ester whose acid component bears a fluorine, nitrogen, oxygen or sulphur atom at the proximity of the carbonyl carbon atom; (b) the mixture of optically active amine and optically active acylated amine is separated so that an enantiomer of amine is produced; (c) if desired the other enantiomer of the amine is extracted from the acylated amine by amide cleavage.

17 Claims, No Drawings

RESOLUTION OF THE RACEMATES OF PRIMARY AND SECONDARY AMINES BY ENZYME-CATALYZED ACYLATION

This application is a 371 of PCT/EP 94/03102, filed Sep. 19, 1994.

BACKGROUND OF THE INVENTION

1. Field of the Invention

The present invention relates to a novel process for resolving the racemates of primary and secondary amines by reacting with an ester in the presence of a hydrolase and subsequently separating one amine which has been enantioselectively acylated from the other, unreacted, enantiomer of the amine.

2. Description of Related Art

Resolution of the racemates of amines by enzyme-catalyzed reaction with esters is known. Kitaguchi et al. (J. Amer. Chem. Soc. 111 (1989) 3094–3095) describe the resolution of racemates of amines with trifluoroethyl butyrate with catalysis by subtilisin. The enantioselectivity of this reaction is, however, greatly dependent on the solvent. Even with the most suitable of the solvents described (3-methyl-3-pentanol) only moderate selectivity is achieved.

WO 91/19002 describes a process for the chiral enrichment of asymmetric primary amines, in which the amines are reacted with ethyl acetate or ethyl butyrate with catalysis by subtilisin. The enantiomeric excesses achieved thereby are, however, unsatisfactory; in addition, long reaction times of up to several weeks are required.

Gotor et al. (J. Chem. Soc. Chem. Commun. (1988) 957–958) describe the enantioselective acylation of 2-amino-1-butanol with ethyl acetate with catalysis by pig pancreatic lipase (PPL). In this case, the ester used (ethyl acetate) is also employed as a solvent. No satisfactory results are obtained on use of other solvents or other enzymes.

Brieva et al. (J. Chem. Soc. Chem. Commun. (1990) 1386–1387) describe the enantioselective synthesis of amides from racemic primary amines by reaction with 2-chloropropionate with catalysis by subtilisin in hexane or Candida cylindracea lipase in 3-methyl-3-pentanol.

Quiros et al. (Tetrahedron: Asymmetry 4 (1993) 1105–1112) describe the lipase-catalyzed synthesis of optically active amides from racemic α-halo-substituted ethyl propionates and primary amines. However, the enantioselectivity achieved with this reaction is unsatisfactory.

Asensio et al. (Tetrahedron Letters 32 (1991) 4197–4198) describe the lipase-catalyzed enantioselective acylation of secondary amines. However, this reaction takes place enantioselectively only with one amine and even there only with moderate success. Other amines show absolutely no enantioselectivity.

The processes hitherto disclosed for enzyme-catalyzed racemate resolution either have too little enantioselectivity or can be carried out only under very specific conditions (solvent, enzyme). In addition, they require long reaction times and enormous amounts of enzyme for the catalysis so that a process based thereon is uneconomic.

SUMMARY OF THE INVENTION

It is an object of the present invention to provide a process for the enzyme-catalyzed resolution of racemates of primary and secondary amines which ensures high enantioselectivity, can be employed in a wide range of reaction conditions and moreover makes do with minimal amounts of catalyst.

We have found that this object is achieved by a process for resolving the racemates of primary and secondary amines by reacting with an ester with specific catalysis by a hydrolase and subsequently separating one amine which has been enantioselectively acylated from the other, unreacted, enantiomer of the amine, which process functions particularly well when the acid component of the ester has an electron-rich heteroatom selected from the group comprising fluorine, nitrogen, oxygen and sulfur atoms in the vicinity of the carbonyl carbon atom.

We have also found a process for preparing acylated primary and secondary amines by reacting the amines with an ester with specific catalysis by a hydrolase, wherein the acid component of the ester has a fluorine, nitrogen, oxygen or sulfur atom in the vicinity of the carbonyl carbon atom.

DESCRIPTION OF THE PREFERRED EMBODIMENTS

Esters suitable for the process according to the invention are those which have an electron-rich heteroatom in the vicinity of the carbonyl carbon in the acid component of the ester.

The heteroatom must have at least one free pair of electrons. It can be a fluorine, nitrogen, oxygen or sulfur atom.

It should be located in the vicinity of the carbonyl carbon. This means that the heteroatom is bonded to a carbon atom in the position alpha, beta or gamma to the carbonyl carbon. Preferred acid components of the ester are those in which the heteroatom is bonded to the C-alpha atom. Oxygen is the preferred heteroatom.

The heteroatom may be linked to other groups, eg. alkyl groups. If the heteroatom is oxygen, for example, an ether moiety is present.

The alcohol component of the ester is not so crucial for the process according to the invention. It is possible to use for this purpose branched and unbranched $C_1$–$C_{10}$-alcohols, which may also be substituted.

Particularly suitable esters are those having the structure

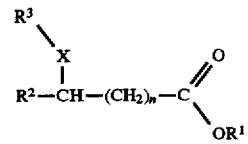

where $R^1$ is $C_1$–$C_{10}$-alkyl, $R^2$ is $C_1$–$C_{10}$-alkyl, H, $R^3$ is H, $C_1$–$C_{10}$-alkyl, or phenyl which is unsubstituted or substituted by $NH_2$, OH, $C_{1-4}$-alkoxy or halogen, X is O, S, $NR^4$, $R^4$ is H, $C_1$–$C_{10}$-alkyl, or phenyl which is unsubstituted or substituted by $NH_2$, OH, $C_{1-4}$-alkoxy or halogen, n is 0, 1 or 2.

Among these, the $C_{1-4}$-alkyl esters of $C_{1-4}$-alkoxyacetic acids, such as ethyl methoxyacetate, are preferred.

A large number of enzymes can be employed as hydrolases in the process according to the invention. Proteases and, in particular, lipases are preferably used. Especially suitable lipases are microbial lipases which can be isolated, for example, from yeasts or bacteria. Particularly suitable lipases are those from Pseudomonas, eg. Amano P or the lipase from Pseudomonas spec. DSM 8246.

Furthermore the lipases Chirazymes L1 to L8, which are commercially available (Boehringer Mannheim), can be advantageously used in the process according to the invention.

The enzyme can be used in native or immobilized form.

Suitable solvents are in general organic solvents. The reaction takes place especially well in ethers, for example in MTBE or THF, or in hydrocarbons such as hexane, cyclohexane, toluene or halohydrocarbons such as methylene chloride.

The primary and secondary amines used can also be amino alcohols.

The reaction of the ester with the racemic amine or amino alcohol with enzyme catalysis is normally carried out at room temperature. The reaction times depend on the substrate and are from 1 to 48 hours. As a rule, longer reaction times are required for secondary amines/amino alcohols than for primary amines/amino alcohols. The lower reactivity of secondary amines may also be compensated by increasing the amount of catalyst compared with the primary amines.

From 1 to 3 mol of ester are added per mole of substrate to be reacted. From 1 to 3 mol of ester are added even when racemic substrates are used.

The amount of enzyme to be added depends on the nature of the hydrolase and the activity of the enzyme preparation. The optimal amount of enzyme for the reaction can easily be established by simple preliminary tests. As a rule, 1000 units of lipase are added per mmol of amine or amino alcohol.

The course of the reaction can easily be followed by conventional methods, for example gas chromatography. In the case of racemate resolution, it is sensible to terminate the reaction when 50% of the racemic amine or amino alcohol has reacted. This usually takes place by removing the catalyst from the reaction medium, for example by filtering off the enzyme.

The enantioselective reaction of the racemic substrate with the ester results in the correspondingly acylated product (amide) of one enantiomer, whereas the other enantiomer remains unchanged. The resulting mixture of amine and amide can easily be separated by conventional methods. Examples of very suitable methods for separating the mixture of amine and amide are extraction or distillation.

The process according to the invention is suitable for acylating all primary and secondary amines. It can also be used to resolve the racemates of virtually all primary and secondary amines. It takes place particularly well in the case of primary arylalkylamines, for example those of the following structures:

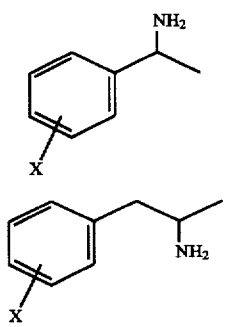

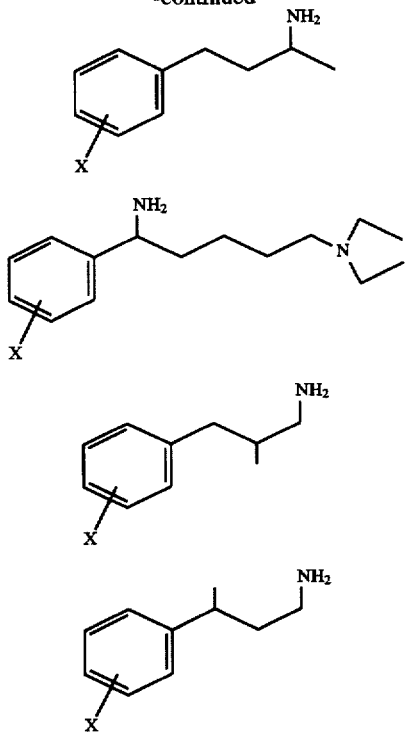

where X is any conventional aromatic substituent, especially halogen, nitro, cyano, $C_1$–$C_4$-alkyl, $C_1$–$C_4$-alkoxy or $C_1$–$C_4$-alkylthio.

The process according to the invention is furthermore suitable for the enantioselective acylation of amino alcohols of the formula

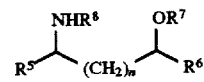

where $R^5$, $R^6$=independently of one another H, branched and unbranched $C_1$–$C_{10}$-alkyl, $C_1$–$C_4$-alkoxycarbonyl, phenyl, phenyl-$C_1$–$C_4$-alkyl, it being possible for the phenyl groups to be substituted by halogen, nitro, cyano, $C_1$–$C_4$-alkyl, $C_1$–$C_4$-alkoxy and $C_1$–$C_4$-alkylthio. $R^5$ and $R^6$ may also be closed to a mono-, bi- or tricyclic system by a carbon chain which may be interrupted by oxygen, sulfur or nitrogen and in turn substituted $R^7$=H, $C_1$–$C_{10}$-alkyl, $C_1$–$C_4$-alkoxycarbonyl $R^8$=H, $C_1$–$C_{10}$-alkyl n=0 or 1.

When the carbon atoms substituted by $OR^7$ or $NHR^8$ are stereogenic centers, the process according to the invention relates both to the syn and to the anti isomers.

Examples of amino alcohols of the above structure are:
2-amino-1-butanol; ephedrine; pseudoephedrine; norephedrine; norpseudoephedrine; tert-leucinol; phenylglycidol; 1,2-diphenylaminoethanol; cis- and trans-2-aminocyclopentanol; cis- and trans-1-amino-2-hydroxyindane; cis- and trans-2-aminocyclohexanol, statine, 2-hydroxy-3-amino-phenylpropionic acid.

Preferred amino alcohols are cis- and trans-1-amino-2-hydroxyindane.

The invention is also suitable for preparing optically active primary and secondary amines from the corresponding racemates by a) enantioselectively acylating a racemic amine or a racemic amino alcohol with an ester whose acid component has a fluorine, nitrogen, oxygen or sulfur atom in the vicinity of the carbonyl carbon atom, in the presence of a hydrolase, b) separating the mixture of optically active amine and optically active acylated amine and obtaining one enantiomer of the amine, c) if required obtaining the other enantiomer of the amine or amino alcohol from the acylated amine by amide cleavage.

The process according to the invention can be made even more economic if, after removal of the required enantiomer, the remaining unwanted enantiomer is racemized and reused in the process. This recycling makes it possible to obtain overall more than 50% of the, required enantiomer from the racemic amine.

The processes according to the invention not only are suitable as processes for producing optically active primary and secondary amines and amino alcohols but can also form part of complicated multistage chemical syntheses, for example in the preparation of pharmaceutical active ingredients or crop protection agents. The following examples illustrate the invention.

EXAMPLE 1

General method for the lipase-catalyzed acylation of amines 10 mmol of the primary or secondary amine are dissolved in MTBE (methyl tert-butyl ether) to give an approximately 10% strength solution. 11 mmol of ethyl methoxyacetate are added to the solution, and the reaction is started by adding 100 mg of lipase (about 1000 U/mg, Pseudomonas spec. DSM 8246). When the reaction is complete (12–48 h depending on the amine), the enzyme is filtered off and the solution is concentrated under reduced pressure. The methoxyacetamides are obtained in a yield of more than 90 percent.

Amines employed:

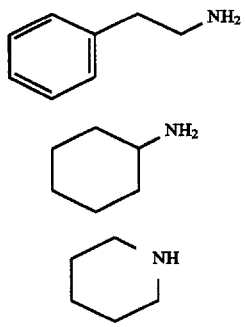

EXAMPLE 2

Method for racemate resolution

The primary or secondary amine is dissolved in MTBE (about 10% by weight). 1 mole of ethyl methoxyacetate is added per 1 mole of racemic amine and then Pseudomonas lipase (DSM 8246) is added and the suspension is stirred at room temperature. About 10,000 units of lipase (10 mg) are added per mmol of amine. After 50% reaction has been reached (checked by gas chromatography), which takes 1–48 h depending on the amine, the enzyme is filtered off. The mixture of amine and acylated amine (amide) is separated by distillation or extraction.

EXAMPLE 3

Racemate resolution 20 g of (1) were reacted with 1 equivalent of (2) in the presence of 2 g of Pseudomonas lipase in MTBE at room temperature as in Example 2. 50% reaction was reached after 22 h.

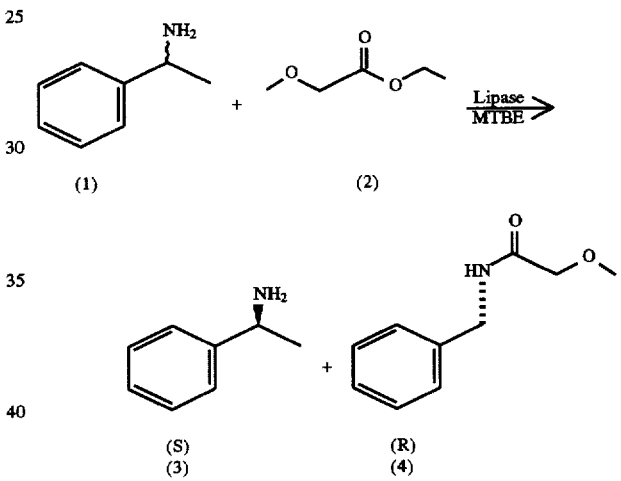

The yield of (3) was 45% (ee>99%), the yield of (4) was 45% (ee>90%).

EXAMPLE 4

Racemate resolution

Various racemate resolutions were carried out as in Example 2. Various amines were employed with diverse reaction conditions. The details are to be found in the table.

TABLE

Reaction scheme: 1-phenylethylamine + methoxyacetate (1 equivalent) → (S)-amine + (R)-N-(methoxyacetyl)-1-phenylethylamide

| No. | Racemic amine (g) | R | MTBE (ml) | Lipase (g; U/mg) | Time (h) | Reaction by GC (%) | ee (amine) (%) | ee (amide) (%) |
|---|---|---|---|---|---|---|---|---|
| 1 | 20 | Et | 180 | 2; 1000 | 7 | 47 | | |
| | | | | | 72 | 57 | >99 | 93 |
| 2 | 5 | Et | 45 | 0.5; 1000 | 3 | 43.6 | | |
| | | | | | 22 | 56.1 | 95 | 96 |
| 3 | 5 | Me | 45 | 0.5; 1000 | 23 | 38.5 | | |
| | | | | | 23 | 51.4 | 79 | 97 |
| 4 | 2.5 | Et | 20 | 0.5; 1000 | 1 | 39.6 | | |
| | | | | | 3 | 50.1 | | |
| | | | | | 24 | 59 | | |
| | | | | | 48 | 59 | >99 | 87 |
| 5 | 2.5 | Et | 20 | 0.5; 1000 | 1 | 41 | | |
| | | | | | 4 | 52 | 85 | 97 |
| 6 | 2.5 | Et | 25 | 0.125; 1000 | 27 | 56.1 | 87 | 97 |
| 7 | 2.5 | Et | 25 | 0.5; 1000 | 21 | 60.1 | 93 | 98 |
| 8 | 2.5 | Et | 10 | 0.25; 1000 | 22 | 50.6 | 82 | 98 |
| 9 | 2.5 | Et | 25 | 0.25; 1000 | 21 | 55.7 | 87 | 99 |
| 10*) | 2.5 | Et | 25 | 0.25; 1000 | 4.5 | 40 | 50 | 97 |
| 11**) | 2.5 | Et | 25 | 0.25; 1000 | 21 | 56.1 | 92 | 98 |
| 12 | 2.5 | Et | 25 | 1; 200 | 2 | 56.1 | 67 | >99 |
| 13 | 2.5 | Me | 25 | 0.5; 200 | 4 | 54.3 | 69 | 99 |
| 14 | 2.5 | Bu | 25 | 0.5; 200 | 4 | 54.2 | 68 | >99 |
| 15***) | 2.5 | Et | 25 | 0.5; 200 | 3 | 54.8 | 57 | >99 |
| 16 | §) Amine 1 | Et | 20 | 0.5; 1000 | 15.5 | 56 | 48 | 52 |
| 17 | §) Amine 2 | Et | 20 | 0.5; 1000 | 3 | 53.6 | 70 | 75 |
| 18 | §) Amine 3 | Et | 25 | 0.25; 1000 | 2 | 53.9 | 83 | >99 |
| 19 | §) Amine 4 | Et | 25 | 0.5; 1000 | 1.5 | 54.6 | 97 | >99 |

*) as Experiment No. 9 but reaction at 50° C.
**) The reaction mixture was shaken not stirred
***) Ethyl butoxyacetate was used as ester in place of the methoxyacetate.
§) 20.6 mmol of each

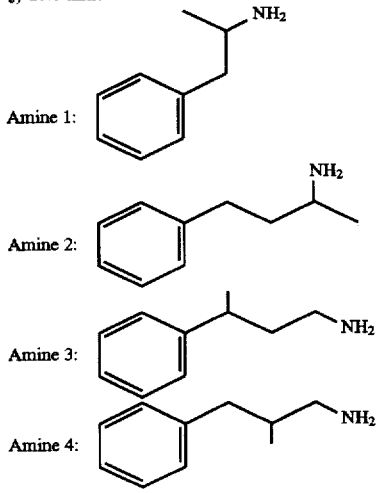

Amine 1, Amine 2, Amine 3, Amine 4

EXAMPLE 5

Resolution of racemic amino alcohols a) to a suspension of 150 mg (1 mmol) of trans-1-amino-2-hydroxyindane and 350 mg (3 mmol) of ethyl methoxyacetate in 10 ml of methyl-tert.-butyl ether were added 9.6 mg of Chirazyme L2, and the mixture was stirred at room temperature. 49% conversion was reached after 41 h. After adding 3 ml of ethanol, the enzyme was filtered off, the filtrate was evaporated to dryness and the residue was taken up in 10 ml of 1N HCl. Extraction ($CH_2Cl_2$), drying ($MgSO_4$) of the organic phase and concentration resulted in the hydroxy amide in the form of white crystals.

Crude yield: 100 mg (42%)

$[\alpha]^{20}_D = -53.9°$ (c=1.65; $CH_2Cl_2$), ee>95%.

b) 150 mg (1 mmol) of cis-1-amino-2-hydroxyindane were reacted with 350 mg (3 mmol) of ethyl methoxyacetate and 50 mg of Chirazyme L1 as in Example 5a). 50% conversion was reached after 48 h. The enantiomeric excess of the hydroxy amide obtained by workup similar to that above was 71%.

We claim:

1. A process for preparing acylated primary and secondary amines which comprises reacting the amines with an ester in the presence of a protease or lipase, wherein the acid component of the ester has a oxygen atom in the α, β or γ position relative to the carbonyl carbon.

2. A process for resolving racemates of primary and secondary amines, which comprises reacting with an ester in the presence of a protease or lipase and subsequently separating one amine which has been enantioselectively acylated from the other, unreacted, enantiomer of the amine, wherein the acid component of the ester has a oxygen atom in the α, β or γ position relative to the carbonyl carbon.

3. A process for preparing optically active primary and secondary amines from the corresponding racemates, which comprises a) enantioselectively acylating a racemic amine with an ester whose acid component has a oxygen atom in the α, β or γ position relative to the carbonyl carbon, in the presence of a protease or lipase, b) separating the mixture of optically active amine and optically active acylated amine and obtaining one enantiomer of the amine, and c) optionally obtaining the other enantiomer of the amine from the acylated amine by amide cleavage.

4. A process as defined in claim 3, wherein step b) or c) is followed by another step in which the unwanted enantiomer is racemized and then returned to the process for resolving the racemate.

5. A process for preparing optically active compounds, which comprises at least in part a process as defined in claim 2.

6. A process as defined in claim 2, wherein the primary or secondary amine is an amino alcohol.

7. A process as defined in claim 6, wherein the amino alcohol is cis- or trans-1-amino-2-hydroxyindane.

8. A process as defined in claim 3, wherein the primary or secondary amine is an amino alcohol.

9. A process as defined in claim 6, wherein the aminoalcohol has the formula

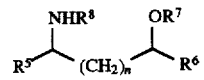

where
R⁵ and R⁶ independently of one another are H, branched and unbranched $C_1$-$C_{10}$-alkyl, $C_1$-$C_4$-alkoxycarbonyl, phenyl, phenyl-$C_1$-$C_4$-alkyl, it being possible for the phenyl groups to be substituted by halogen, nitro, cyano, $C_1$-$C_4$-alkyl, $C_1$-$C_4$-alkoxy and $C_1$-$C_4$-alkylthio, where R⁵ and R⁶ may also be closed to a mono-, bi- or tricyclic system by a carbon chain which may be interrupted by oxygen, sulfur or nitrogen, R⁷ is H, $C_1$-$C_{10}$-alkyl or $C_1$-$C_4$-alkoxycarbonyl, R⁸ is H or $C_1$-$C_{10}$-alkyl, and n is 0 or 1.

10. A process as defined in claim 1 wherein the ester is ethyl methoxyacetate.

11. A process as defined in claim 2 wherein the ester is ethyl methoxyacetate.

12. A process as defined in claim 3 wherein the ester is ethyl methoxyacetate.

13. A process as defined in claim 4 wherein the ester is ethyl methoxyacetate.

14. A process as defined in claim 5 wherein the ester is ethyl methoxyacetate.

15. A process as defined in claim 6 wherein the ester is ethyl methoxyacetate.

16. A process as defined in claim 7 wherein the ester is ethyl methoxyacetate.

17. A process as defined in claim 9 wherein the ester is ethyl methoxyacetate.

* * * * *